United States Patent [19]

Kim et al.

[11] Patent Number: 5,292,733
[45] Date of Patent: Mar. 8, 1994

[54] CEPHALOSPORIN COMPOUNDS

[75] Inventors: Yong Z. Kim; Hun S. Oh; Jae H. Yeo; Jong C. Lim; Won S. Kim; Chan S. Bang; Hyeon J. Yim, all of Daejeon, Rep. of Korea

[73] Assignee: Lucky Limited, Rep. of Korea

[21] Appl. No.: 866,156

[22] Filed: Apr. 9, 1992

[30] Foreign Application Priority Data

Apr. 12, 1991 [KR] Rep. of Korea .................. 91-5843
Apr. 23, 1991 [KR] Rep. of Korea .................. 91-6494

[51] Int. Cl.$^5$ .................. C07D 501/36; A61K 31/545
[52] U.S. Cl. .................................. 514/206; 540/226; 540/227
[58] Field of Search ............. 540/226, 227; 514/202, 514/206

[56] References Cited

U.S. PATENT DOCUMENTS 5,142,041 8/1992 Kim et al. .................. 540/226

Primary Examiner—Nicholas S. Rizzo
Attorney, Agent, or Firm—James D. Hall; Thomas J. Dodd; R. Tracy Crump

[57] ABSTRACT

The present invention relates to a cephalosporin compound including the pharmaceutically acceptable non-toxic salts, physiologically hydrolyzable esters, hydrates and solvates thereof of the formula(I) and its isomers:

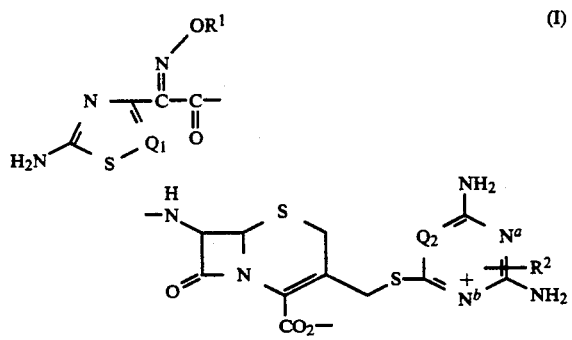

wherein:

$R^1$ is a $C_{1-4}$ alkyl, $C_{3-4}$ alkenyl, $C_{3-4}$ alkynyl or —C($R^3$)($R^4$)COOH wherein $R^3$ and $R^4$, which may be the same or different, are hydrogen, $C_{1-4}$ alkyl group, or constitute a $C_{3-7}$ cycloalkyl group with the carbon atoms to which $R^3$ and $R^4$ are attached;

$R^2$, which may be attached to $N^a$ or $N^b$, is a $C_{1-4}$ alkyl, $C_{3-4}$ alkenyl, $C_{3-7}$ cycloalkyl, aryl or amino group; and $Q_1$ and $Q_2$, which may be the same or different, are CH or N.

5 Claims, No Drawings

CEPHALOSPORIN COMPOUNDS

FIELD OF THE INVENTION

The present invention relates to novel cephalosporin compounds, pharmaceutically acceptable non-toxic salts thereof, and physiologically hydrolyzable esters, hydrates and solvates thereof, which possess potent and broad antibacterial activities. The invention also relates to processes for preparing these compounds and to pharmaceutical compositions containing them as active ingredients.

DESCRIPTION OF THE PRIOR ART

Antibiotics of cephalosporin series are widely used in therapy for treatment of diseases which are caused by general pathogenic bacteria in human beings and animals. It has been known that such antibiotics are useful for the treatment of diseases caused by bacteria exhibiting resistance to other antibiotics, e.g., penicillin-resistant bacteria, and for treatment of penicillin-sensitive patients.

In most circumstances, it is desirable to employ antibiotics possessed with broad antibacterial activities, e.g., against both Gram-positive and Gram-negative bacteria. In this regard, there were many studies made in developing a variety of cephalosporin antibiotics with such broad-spectrum antibiotic activities.

For example, GB Patent No. 1,399,086 disclosed 7β-acylamido-ceph-3-em-4-carboxylic acids having the formula(A) of:

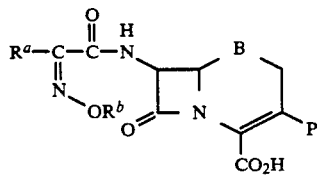

wherein:
$R^a$ is a hydrogen or an organic group;
$R^b$ is an etherifying monovalent organic group linked to the oxygen atom through a carbon atom;
B is S or S→O; and
P is an organic group.

Stimulated by the discovery of these compounds, there followed many attempts to develop antibiotic compounds having improved properties with respect to certain microorganisms, especially against Gram-negative bacteria. Such efforts resulted in the development of, e.g., those compounds disclosed in GB Patent No. 1,522,140, which have the following formula(B) and exist as syn isomers or as a mixture of syn and anti isomers wherein the syn isomers are present in at least 90%.

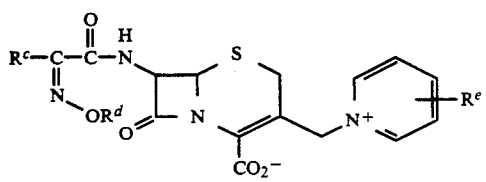

wherein:
$R^c$ is a furyl or thienyl group;
$R^d$ is a $C_{1-4}$ alkyl, $C_{3-7}$ cycloalkyl, furylmethyl or thienylmethyl group; and
$R^e$ is a hydrogen or a carbamoyl, carboxy, carboxymethyl, sulfonyl or methyl group.

Recently, further efforts were made to prepare new and improved antibiotics, typically by way of introducing an acylamido group into the 7-position and certain other groups into the 3-position of the cephem nucleus as shown in the foregoing formula(B).

For example, BE Patent No. 852,427 disclosed cephalosporin compounds prepared by substituting $R^a$ in the formula(A) with various organic group including 2-aminothiazol-4-yl and by way of attaching an aliphatic hydrocarbon, which hydrocarbon may further be substituted with a carboxy group, to the oxygen atom in the oxyimino group.

European Patent Application No. 47,977 disclosed cephalosporin compounds having the following formula(C) of

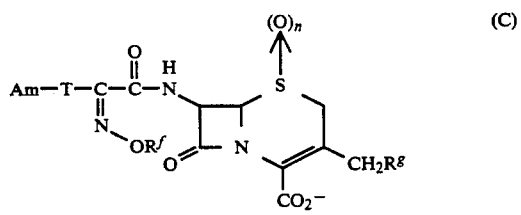

wherein:
n is 0 or 1;
Am is an optionally substituted amino group;
T is a thiodiazolyl group (which is attached to other group by its two carbon atoms);
$R^f$ is a hydrogen or a cycloalkyl, optionally substituted alkyl or carbamoyl group; and
$R^g$ is an optionally substituted thiazolium or pyrazolium, tri(lower)alkyl ammonium, or pyridinium group having the formula of

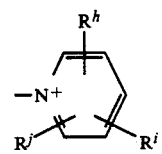

wherein:
$R^h$ is an (lower)alkyl substituted with cycloalkyl, methyl, hydroxy, alkoxy, halogen, cyano, carbamoyl, carboxy or sulfonyl, (lower)alkenyl, (lower)alkylthio optionally substituted with carboxy, amino optionally monosubstituted by (lower)alkyl, (lower)alkanoyl or aminobenzenesulfonyl, di(lower)alkylamino, carbamoyl substituted with (lower) alkyl, hydroxy, (lower)alkyl, (lower)alkoxy, hydroxy or cyano, di(lower)alkylcarbamoyl, thiocarbamoyl, cycloalkyl, phenyl, hydroxy, (lower)alkoxy, halogen, (lower)alkoxycarbonyl, (lower)alkanoyloxy, (lower)alkanoyl, carboxy, sulfocyano, nitro or hydroxysulfo(lower)alkyl group;
$R^i$ is a hydrogen or a carbamoyl or the same as $R^h$; and
$R^j$ is a hydrogen or the same as $R^h$.

U.S. Pat. No. 4,390,534 disclosed the cephem compounds of the formula(D) of:

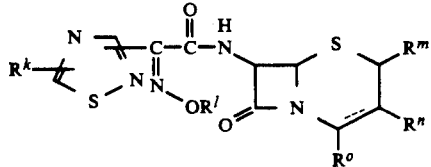

(D)

wherein:

$R^k$ is an amino or protected amino group;

$R^l$ is a hydrogen or an acyl, optionally substituted aryl, substituted alkyl, alkenyl, alkynyl, optionally substituted cycloalkyl, cycloalkenyl or 5-membered heterocyclic ring containing oxygen or sulfur substituted with hydroxy;

$R^m$ is a hydrogen or an alkyl group;

$R^n$ is a hydrogen or an acyloxyalkyl, alkylthioalkyl, optionally substituted pyridinium alkyl, optionally substituted heterocyclic thioalkyl, alkyl, halogen, hydroxy or optionally substituted thiazolium alkyl group;

$R^o$ is a carboxy or protected carboxy group, provided that $R^o$ is a carboxy if $R^n$ is an optionally substituted pyridinium alkyl or optionally substituted thiazolium alkyl group; and The dotted line represents a single or double bond. As shown above, no prior art literature has disclosed or suggested the possibility of employing a (3-substituent-2,6-diaminopyrimidinium-4-yl)thiomethyl group as a substituent in 3-position of the cephem nucleus.

SUMMARY OF THE INVENTION

The present inventors have studied for a long time in search for a cephalosporin compound which has a broad spectrum of antibiotic activity; and, specifically, for an antibiotic effective against a variety of Gram-negative bacteria including genus Pseudomonas which exhibits very strong resistance to various antibiotics.

As a result, the present inventors have discovered that cephalosporin compounds with a diaminopyrimidinium thiomethyl or triazinium thiomethyl group in 3-position and having a certain group in 7-β-position of the cephem nucleus exhibit strong antibacterial activities in a broad spectrum.

Accordingly, the primary objective of the present invention is to provide novel cephalosporin compounds of formula(I):

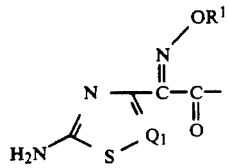

(I)

-continued

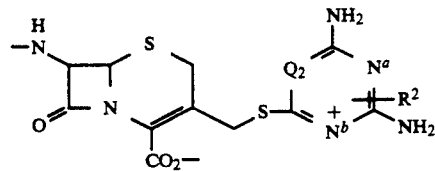

wherein:

$R^1$ is a $C_{1-4}$ alkyl, $C_{3-4}$ alkenyl, $C_{3-4}$ alkynyl or —C($R^3$)($R^4$)— COOH wherein $R^3$ and $R^4$, which may be the same or different, are a hydrogen or a $C_{1-4}$ alkyl group, or constitute a $C_{3-7}$ cycloalkyl group with the carbon atoms to which $R^3$ and $R^4$ are linked;

$R^2$, which may be attached to $N^a$ or $N^b$, is a $C_{1-4}$ alkyl, $C_{3-4}$ alkenyl, $C_{3-7}$ cycloalkyl, aryl or amino group; and $Q_1$ and $Q_2$, which may be the same or different, are CH or N.

More preferred cephalosporin compounds of the present invention are the compounds of formula(I), wherein $R^1$ is a methyl, ethyl, propyl, propenyl, propynyl, —CH$_2$COOH, —CH(CH$_3$)COOH, or —C(CH$_3$)$_2$COOH; and $R_2$ is a methyl, ethyl, phenyl or amino group.

Another aspect of the present invention involves novel processes for preparing the cephalosporin compounds of formula(I).

A further feature of the present invention relates to the pharmaceutically acceptable non-toxic salts, physiologically hydrolyzable esters, hydrates and solvates of the compounds of formula(I) and processes for preparing these compounds.

A still further novel contribution of the present invention resides in the formulation of pharmaceutical compositions comprising one or more of the cephalosporin compounds represented by formula(I) and their pharmaceutically acceptable derivatives.

DETAILED DESCRIPTION OF THE INVENTION

The novel cephalosporin compounds of formula(I) include both syn isomers and mixtures of syn and anti isomers, with respect to the radical, —O—C($R^3$)($R^4$)—COOH, which contain at least 90% of the syn isomer or not more than 10% of the anti isomer.

In addition, the compounds of formula(I) according to the present invention may exist in tautomeric forms and such tautomers are also included within the scope of the invention. Namely, when $Q_1$ of formula(I) is CH, the aminothiazolyl group undergoes tautomerism to form an iminothiazolinyl group, its tautomer, as follows:

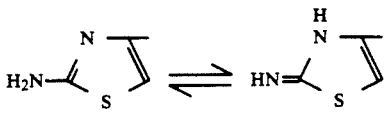

When $Q_1$ of formula(I) is N, the aminothiadiazolyl group forms iminothiadiazolinyl group, its tautomers, as follows:

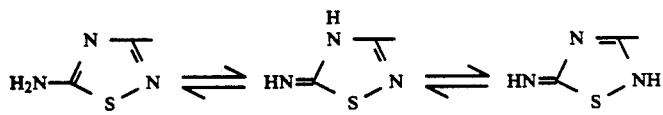

The compounds of formula(I) also include the resonance isomers. Therefore, for instance, if the compounds of formula(I) have a substituent in $N^b$, the compounds in accordance with the present invention include the following structures of formula(I)' and (I)":

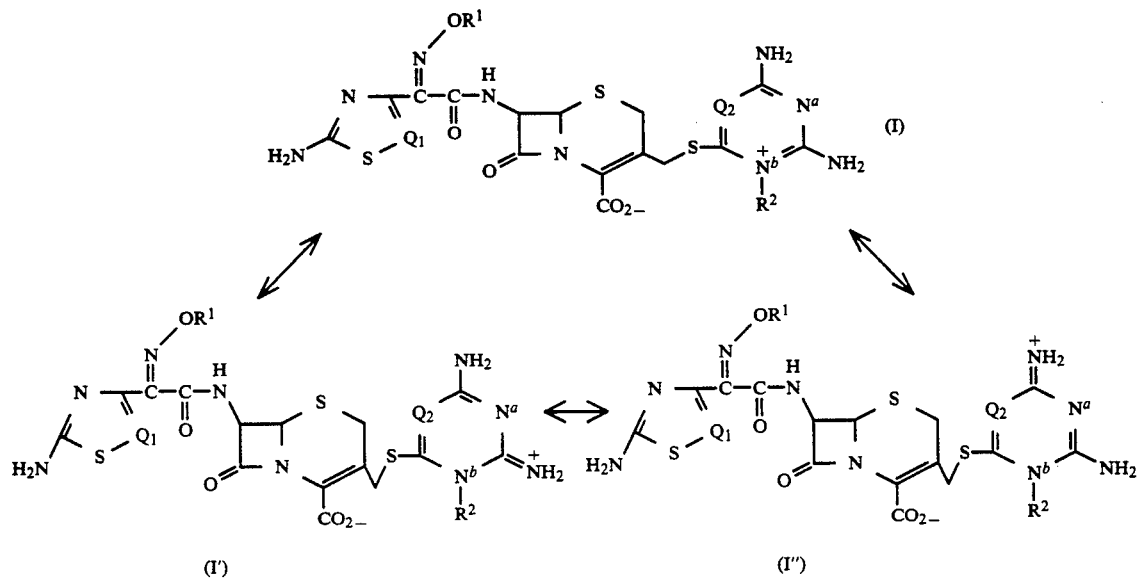

Similarly, there are also the resonance isomers of the compounds of formula (I) if $N^a$ is substituted.

Furthermore, the present invention encompasses, within its scope, those pharmaceutically acceptable non-toxic salts, physiologically hydrolyzable esters, solvates and hydrates of the compounds of formula (I). Suitable pharmaceutically acceptable salts of the cephalosporin compounds (I) are conventional non-toxic salts and may include inorganic salts, for example, metal salts such as alkali metal salts (e.g., sodium salt, potassium salt, etc.), and alkaline earth metal salts (e.g., calcium salt, magnesium salt, etc.), ammonium salt, etc.; organic salts, for example, an organic amine salt (e.g., trimethylamine salt, N-methylglucamine salt, diethanolamine salt, triethanolamine salt, triethylamine salt, pyridine salt, procaine salt, picoline salt, dicyclohexylamine salt, N,N'-dibenzylethylenediamine salt, tris(hydroxymethylamino)methane salt, phenylethylbenzylamine salt, dibenzylethylenediamine salt, etc.); organic carboxylic or sulfonic acid salts (e.g., formate, acetate, maleate, tartrate, methanesulfonate, benzenesulfonate, toluenesulfonate, etc.); inorganic acid salts (e.g., hydrochloride, hydrobromide, sulfate, phosphate, etc.); salts with basic or acidic amino acids (e.g., arginine, aspartic acid, glutamic acid, lysine, etc.); more preferably, alkali metal salts, alkaline earth metal salts, inorganic acid salts, organic carboxylic acid salts and salts with basic or acidic amino acids; and most preferably, sodium salt, potassium salt, hydrochloride and sulfate.

Above pharmaceutically acceptable non-toxic salts may be prepared by reacting the compounds of the formula (I) with one to four equivalents of corresponding acids or bases to the salts mentioned above in the presence of a solvent which may be water, or a mixture of water and water-miscible solvent (e.g., methanol, ethanol, acetonitrile, acetone, etc.).

The physiologically hydrolyzable esters of the compounds (I) may include, for example, methoxycarbonyloxymethyl, 1-methoxycarbonyloxy-1-ethyl, indanyl, phthalidyl, methoxymethyl, pivaloyloxymethyl, glycyloxymethyl, phenylglycyloxymethyl or 5-methyl-2-oxo-1,3-dioxolan-4-yl esters, and other physiologically hydrolyzable esters which have been widely used in the technical fields of penicillin and cephalosporin antibiotics; more preferably, methoxycarbonyloxymethyl, 1-methoxycarbonyloxy-1-ethyl, methoxymethyl or pivaloyloxymethyl; and most preferably, methoxycarbonyloxymethyl or methoxymethyl.

These esters can be prepared in accordance with known methods, e.g., by reacting the compounds of formula (I) with corresponding alkyl halides (e.g., methoxymethyl chloride or methoxycarbonyloxymethyl chloride) in the presence of a base (e.g., triethylamine, pyridine or sodium bicarbonate).

Exemplary solvates of the cephalosporin compounds of formula (I) may include solvates with water-miscible solvents, e.g., methanol, ethanol, acetone or acetonitrile; and more preferably, ethanol.

The present invention also includes within its scope pharmaceutical compositions comprising one or more of the compounds (I) as active ingredients, in association with pharmaceutically acceptable carriers, excipients or other additives, if necessary.

The antibiotic compounds (I) of the invention may be formulated for administration in unit dose or multi-dose containers. The compositions may take various forms such as solution, suspension or emulsion in an oily or aqueous vehicle, which can contain conventional additives such as a dispersant, suspending agent, stabilizer and the like. Alternatively, the active ingredient may be formed into a dried powder that can be normally dissolved in an aqueous solution of sterile pyrogen-free water before use. The compounds (I) may be also formulated into suppositories containing conventional suppository bases such as cocoa butter or other glycerides.

The pharmaceutical compositions in a unit dose form may preferably comprise about 50 to 1,500 mg of the active ingredient, depending on the age and body weight of the patient, the nature and severity of the illness, and so on. In general, it has been shown advantageous to administer the active compounds in an amount ranging from 500 to 5,000 mg per day in order to achieve the desired results, depending on the routes and frequency of admini-stration. In case of intramuscular or intravenous administration for adult human treatment, the dosage of about 150 to 3,000 mg per day is thought to be sufficient, although it may vary in case of treatment for specific infections caused by certain strains.

If desired, the compounds (I) can be administered in combination with other antibiotics such as penicillin or other cephalosporins.

The compounds of the present invention, as described above, exhibit potent and broad antibacterial activities against Gram-positive bacteria and a variety of Gram-negative bacteria as well, particularly against Pseudomonas. Also, these compounds have high stability to $\beta$-lactamases produced by a number of Gram-negative bacteria.

A compound of formula (I) may be prepared by comprising the reaction of a compound of formula (II) in the presence of a solvent, with a compound of formula (III) as follows:

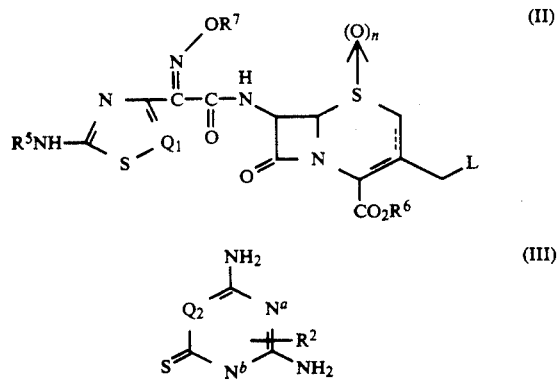

wherein:
$R^2$, $Q_1$ and $Q_2$ have the same meanings as defined above;
n is 0 or 1;
$R^5$ is a hydrogen or an amino protecting group;
$R^6$ is a hydrogen or a carboxyl protecting group;
$R^7$ is a $C_{1-4}$ alkyl, $C_{3-4}$ alkenyl, $C_{3-4}$ alkynyl or —$C(R^3)(R^4)$—$COOR^8$ wherein $R^3$ and $R^4$, which may be the same or different, are hydrogen, a $C_{1-4}$ alkyl or constitute a $C_{3-7}$ cycloalkyl group with the carbon atoms to which they are linked, and $R^8$ is a hydrogen or a carboxyl protecting group; and
L is a leaving group.

The amino protecting group in $R^5$ above may include acyl, substituted or unsubstituted aryl(lower)alkyl (e.g., benzyl, diphenylmethyl and triphenylmethyl), (lower-)alkoxyaryl (e.g., 4-methoxybenzyl), halo(lower)alkyl (e.g., trichloromethyl and trichloroethyl), tetrahydropyranyl, substituted phenylthio, substituted alkylidene, substituted aralkylidene or substituted cycloalkylidene. The acyl group as an amino protecting group may include, for example, $C_{1-6}$ alkanoyl (e.g., formyl and acetyl), $C_{2-6}$ alkoxycarbonyl (e.g., methoxycarbonyl and ethoxycarbonyl), (lower) alkanesulfonyl (e.g., methanesulfonyl and ethanesulfonyl), or aryl (lower)alkoxycarbonyl (e.g., benzyloxycarbonyl), where the acyl group can be substituted with 1-3 substituent(s) such as halogen, hydroxy, cyano or nitro. In addition, the amino protecting group may include reaction products obtained from amino groups and silane, boron or phosphorus compounds.

The carboxyl protecting group of $R^6$ or $R^8$ may include, for example, (lower)alkylesters(e.g., methylester and t-butylester), (lower)alkenylesters(e.g., vinylester and allylester), (lower) alkoxy(lower)alkylesters(e.g., methoxymethylester), (lower)alkylthio(lower)alkylesters(e.g., methylthiomethylester), halo(lower) alkylesters(e.g., 2,2,2-trichloroethylester), substituted or unsubstituted aralkylesters(e.g., benzylester and p-nitrobenzylester) or silylesters, which can be selected after consideration of the chemical property of the desired compounds(I).

The leaving group L in formula(II) may include, for example, halogen such as chlorine or bromine, a (lower-)alkanoyloxy group such as acetoxy, a (lower)alkanesulfonyloxy group such as methanesulfonyloxy, an arenesulfonyloxy group such as p-toluenesulfonyloxy, an alkoxycarbonyloxy group and the like.

The term "lower" as used hereinabove and elsewhere in this specification, for example in reference to "lower alkyl", encompasses groups having 1 to 6 carbon atoms, more preferably, 1 to 4 carbon atoms.

In the preparation of the objective compounds of formula (I), the compounds of the formula(III) are used preferably in an amount ranging from 1 to 2 molar equivalents based on the compounds of the formula(II).

Amino or carboxyl protecting groups can be readily removed by any of the conventional deprotection methods which are well known in the field of cephalosporin antibiotics. For example, acid- or base-hydrolysis or reduction is generally applicable.

Reduction of S-oxide can be conventionally carried out, for example, by adding potassium iodide and acetyl chloride to the reactants, followed by quenching the reaction mixture with sodium m-bisulfite.

The reaction for introducing the compounds(III) into the 3-position of the compounds(II) to prepare the compounds(I) is carried out in the presence of a solvent such as water, a water-miscible solvent or a mixture thereof, wherein the pH of the reaction solution may range from 5 to 8, more preferably, from 6 to 7.5; and the temperature may range from 20° to 100° C., more preferably from 60° to 80° C.

The starting materials of the compounds(II) are known intermediates conventionally employed for the preparation of cephalosporin compounds. The dotted line of formula(II) represents a single or double bond; and, therefore, the compounds of formula (II) may be the compounds of formula(II-a), or the compounds of formula(II-b), or mixtures thereof:

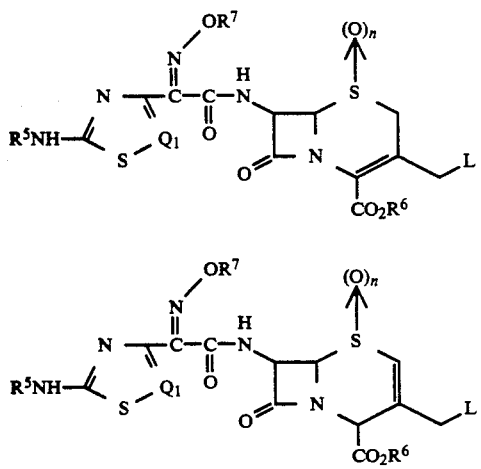

wherein:
n, $R^5$, $R^6$, $R^7$, $Q_1$ and L have the same meanings as defined before.

Another starting materials of formula(III) may be prepared by the following scheme (A) or (B), depending on whether $Q_2$ is CH or N.

The compounds of formula(III) wherein $Q_2$ is CH, which is referred to as formula(IIIa) hereinafter, may be prepared by following the scheme(A):

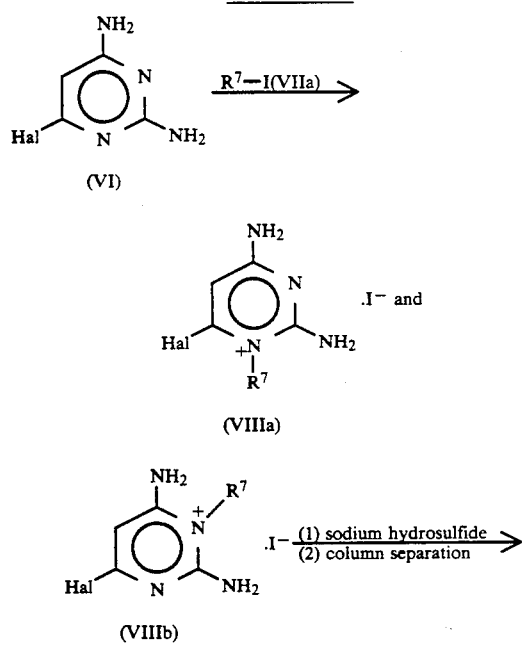

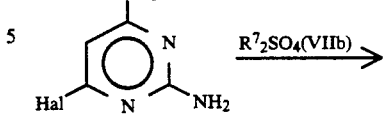

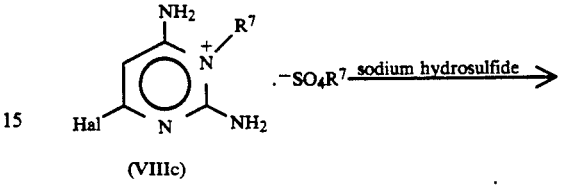

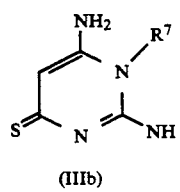

wherein:
$R^7$ has the same meaning as previously defined; and
Hal is a halogen atom.

A compound of formula(VI) is heated with a compound of formula(VIIa) or (VIIb) at reflux in an inert solvent such as tetrahydrofuran to prepare a mixture of pyrimidinium iodides of formula(VIIIa) and formula(VIIIb) or pyrimidinium sulfate of formula (VIIIc), which is subsequently heated at reflux with sodium hydrosulfide and, if necessary fractionated on the silica gel chromatography to obtain the desired starting material of formula (IIIa) or (IIIb).

Another starting materials of formula(IIIc) wherein $Q^2$ is N, which is referred to as formula(IIIc) hereinafter, may be prepared by the following scheme(B):

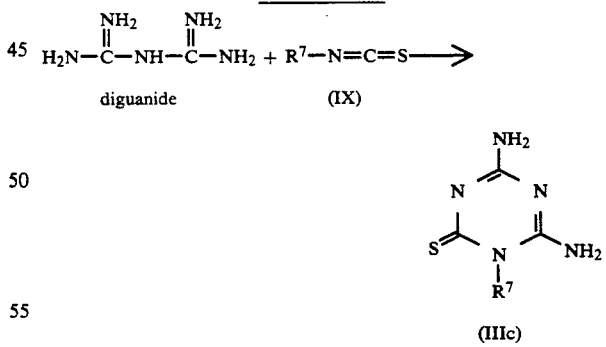

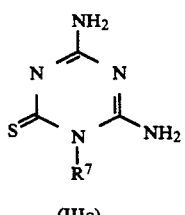

wherein $R^7$ has the same meaning as previously defined.

The desired compounds of formula(IIIc) may be prepared by reacting diguanide with an isothiocyanate of formula(IX), preferably in dimethylformamide at a temperature ranging from a room temperature to 100° C. for 30 minutes to 1 hour.

To stabilize the reaction products and their intermediates, one or more salts selected from the group consisting of sodium iodide, potassium iodide, sodium bromide, potassium bromide and potassium thiocyanate can be used as a stabilizer.

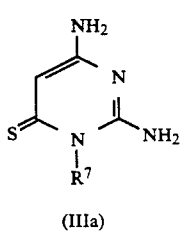

The separation and purification of the compounds(I) can be carried out by using a conventional method such as recrystallization, column chromatography over silica gel or ion-exchange chromatography.

The following Preparation Examples and Examples illustrate how some of the starting materials of formula(III) and of the compounds of formula(I) can be prepared.

PREPARATION EXAMPLE 1

Preparation of 2,6-diamino-3-methyl-4(1H)pyrimidinethione

To a solution of 14.45 g of 2,6-diamino-4-chloro-1,3-pyrimidine dissolved in 100 ml of tetrahydrofuran was added 70 g of methyl iodide. The reaction mixture was refluxed for 10 hours and cooled to 0° C. to produce precipitates.

After the mixture was filtered, the solids were washed with tetrahydrofuran and dried to obtain 25.6 g of 2,6-diamino-4-chloro-3-methyl-1-pyrimidinium iodide.

NMR($\delta$, DMSO-$d_6$):8.2(d, 4H), 6.19(s, 1H), 3.38(s, 3H)

14.3 g of 2,6-diamino-4-chloro-3-methyl-1-pyrimidinium iodide so obtained and 14 g of sodium hydrosulfide hydrate were mixed to 75 ml of methanol. The reaction mixture was refluxed for 1 hour and the undissolved materials was removed rapidly. After removing solvent, the residues were fractionated on the chromatography using mixtures of dichloromethane and methanol (4:1) as an eluent, to give 4.1 g of the title compound having the characteristics of:

$R_f$=0.2
m.p.>200° C.(dec.)
NMR($\delta$, DMSO-$d_6$); 7.15(s, 2H), 6.92(s, 2H), 5.90(s, 1H), 3.28(s, 3H)

PREPARATION EXAMPLE 2

Preparation of 2,6-diamino-3-ethyl-4(1H)pyrimidinethione

To a solution of 14.45 g of 2,6-diamino-4-chloro-1,3-pyrimidine dissolved in 100 ml of tetrahydrofuran was added 77 g of ethyliodide. The reaction mixture was refluxed for 8 hours and cooled to 0° C. to produce precipitates.

After the mixture was filtered, the solids were washed with tetrahydrofuran and dried to obtain 25 g of 2,6-diamino-4-chloro-3-ethyl-1-pyrimidinium iodide.

NMR($\delta$, DMSO-$d_6$): 8.2(d, 4H), 6.20(s, 1H), 3.54(q, 2H), 1.40(t, 3H)

15.02 g of the compound so obtained and 14 g of sodium hydrosulfide hydrate were mixed to 75 ml of methanol. The reaction mixture was refluxed for 1 hour and the undissolved materials were removed rapidly.

After the solvent was removed, the residues were fractionated on the chromatography using mixture of dichloromethane and methanol (4:1) as an eluent, to give 4.3 g of the title compound having the characteristics of:

m.p.>196° C.(dec.)
NMR($\delta$, DMSO-$d_6$): 7.16(s, 2H), 6.92(s, 2H), 5.90(s, 1H), 4.05(q, 2H), 1.30(t, 3H)

PREPARATION EXAMPLE 3

Preparation of 2,6-diamino-1-methyl-4(1H)pyrimidinethione

To a solution of 14.45 g of 2,6-diamino-4-chloro-1,3-pyrimidine dissolved in 100 ml of tetrahydrofuran was added 38 g of dimethylsulfate. The reaction mixture was refluxed for 10 hours, cooled to 0° C. to produce precipitates. After the mixture was filtered, the solids were washed with tetrahydrofuran and dried to obtain 25.6 g of 2,6-diamino-4-chloro-1-pyrimidinium methanesulfonate.

NMR($\delta$, DMSO-$d_6$): 8.2(d, 4H), 6.30(s, 1H), 3.52(s, 3H), 3.38(s, 3H)

14.3 g of the compound so obtained and 14 g of sodium hydrosulfide hydrate were mixed to 75 ml of methyl alcohol. The reaction mixture was refluxed for 1 hour and the undissolved materials were removed rapidly. After solvent was removed, the residues were fractionated on chromatography using mixture of dichloromethane and methanol (5:1) as an eluent, to give 4.1 g of the title compound having the characteristics of:

m.p.>210° C.(dec.)
NMR($\delta$, DMSO-$d_6$): 7.05(s, 2H), 6.42(s, 2H), 5.96(s, 1H), 3.69(s, 3H)

PREPARATION EXAMPLE 4

Preparation of 2,6-diamino-1-ethyl-4(1H)pyrimidinethione

To a solution of 14.45 g of 2,6-diamino-4-chloro1,3-pyrimidine dissolved in 100 ml of tetrahydrofuran was added 38 g of diethylsulfate. The reaction mixture was refluxed for 8 hours and cooled to 0° C. to produce precipitates. After the mixture was filtered, the solids were washed with tetrahydrofuran and dried to obtain 25 g of 2,6-diamino-4-chloro-1-ethyl-pyrimidinium methanesulfonate.

NMR($\delta$, DMSO-$d_6$): 8.1~9.0(bd, 4H), 6.42(s, 1H), 3.85 (q, 2H), 3.38(s, 3H), 1.42(t, 3H)

15.02 g of the compound so obtained and 14 g of sodium hydrosulfide hydrate were mixed to 75 ml of methyl alcohol. The reaction mixture was refluxed for 1 hour and the undissolved materials were removed rapidly. After solvent was removed, the residues were fractionated on to the chromatography and the same procedures were followed as Preparation Example 1 to obtain 4.3 g of the title compound having the characteristics of:

m.p.>206° C.(dec.)
NMR($\delta$, DMSO-$d_6$): 7.06(s, 2H), 6.50(s, 2H), 5.94(s, 1H), 4.19(q, 2H), 1.42(t, 3H)

PREPARATION EXAMPLE 5

Preparation of 4,6-diamino-1-methyl-S-triazine-2-thione

To 12 of dry dimethylformamide were dissolved 1.52 g of diguanide and 1.1 g of methylisothiocyanate, and the solution was heated at 100° C. for 30 minutes to produce white precipitates. After filtering off the precipitates rapidly, the filtrate was added to 500 ml of ice water to produce precipitates, which was subsequently filtered and recrystalized with 25 ml of 50% ethanol to obtain 2 g of the title compound having the characteristics of:

m.p.: 295°~297° C.(dec.)

NMR(δ, DMSO-d6): 7.59(bs, 2H), 7.00(bd, 2H), 3.69(s, 3H)

PREPARATION EXAMPLE 6

Preparation of 4,6-diamino-1-ethyl-S-triazine-2-thione

To 15 ml of dry dimethylformamide were dissolved 1.52 g of diguanide and 1.31 g of ethylisothiocyanate, and the solution was heated at 100° C. for 4 hours. After cooling, the solution was added to 60 ml of water to produce white precipitates, which subsequently was dried to obtain 2.7 g of the title compound having the characteristics of:

m.p.: 282°~283° C.(dec.)

NMR(δ, DMSO-d6): 7.00(bd, 2H), 4.00(q, 2H), 1.25(t, 3H)

PREPARATION EXAMPLE 7

Preparation of 4,6-diamino-1-phenyl-S-triazine-2-thione

To 25 ml of dry dimethylformamide were dissolved 2.0 g of diguanide and 2.7 g of phenyl isothiocyanate and the solution was placed at 40°~50° C. for 30 minutes. The solution was added to 200 ml of ice water to produce white precipitates, which subsequently was filtered and dried to obtain 4.05 g of the title compound having the characteristics of:

m.p.: 286°~298° C.(dec.)

NMR(δ, DMSO-d6): 7.4~7.7(m. 5H), 7.8(s, 2H), 7.2(d, 2H)

EXAMPLE 1

Synthesis of (6R,7R)-7-[(Z)-2-(2-aminothiazol-4-yl)-2-(carboxyprop-2-oxyimino)acetamido]-3-(2,6-diamino-3-methylpyrimidinium-4-yl)thiomethyl-3-cephem-4-carboxylate (I-1)

To a solution of 500 mg of (6R,7R)-3-acetoxymethyl-7[(Z)-2-(2-aminothiazol-4-yl)-2-(carboxyprop-2-oxyimino)acetamido]-3-cephem-4-carboxylic hydrochloride suspended in 5 ml of distilled water were added 200 mg of the title compound of Preparation Example 1 and 800 mg of potassium iodide and the reaction solution was heated to 70° C. while adjusting pH to 7.1~7.2 with addition of aqueous sodium bicarbonate solution. The resultant solution was stirred for 4 hours, cooled to room temperature and adjusted to pH 3 to 3.5 with 2N aqueous hydrochloric acid solution to produce precipitates, which were washed with 5 ml of distilled water after filtration. The filtered solids was dissolved and fractionated on the chromatography on silica gel using mixtures of acetonitrile and distilled water (5:1) as an eluent, to give 330 mg of the title compound as a light yellow solid having the characteristics of:

m.p.>175° C.(dec.)

NMR(δ, D2O): 6.99(s, 1H), 5.80(d, 1H), 5.16(d, 1H), 3.6~4.8(dd, 2H), 3.4~3.8(dd, 2H), 3.49(s, 3H), 1.49(s, 6H)

IR(KBr, cm$^{-1}$): 1766(β-lactam), 1669, 1615, 1558

EXAMPLE 2

Synthesis of (6R,7R)-7-[(Z)-2-(2-aminothiazol-4-yl)-2-(carboxyprop-2-oxyimino)acetamido]-3-(2,6-diamino-3-ethylpyrimidinium-4-yl)thiomethyl-3-cephem-4-carboxylate (I-2)

To a solution of 500 mg of (6R,7R)-3-acetoxymethyl-7[(Z)-2-(2-aminothiazol-4-yl)-2-(carboxyprop-2-oxyimino)acetamido]-3-cephem-4-carboxylic hydrochloride suspended in 5 ml of distilled water were added 200 mg of the title compound of Preparation Example 2 and 800 mg of potassium iodide. Subsequently, the same procedures as Example 1 were repeated to obtain 300 mg the title compound having the characteristics of:

m.p.>163° C.(dec.)

NMR(δ, D2O): 6.99(s, 1H), 6.19(s, 1H), 5.79(d, 1H), 5.16(d, 1H), 3.7~4.8(dd, 1H), 3.41~4.05(dd, 1H), 3.61(q, 2H), 1.52(s, 6H), 1.21(t, 3H)

IR(KBr, cm$^{-1}$): 1770(β-lactam), 1680, 1590

EXAMPLE 3

Synthesis of (6R,7R)-7-[(Z)-2-(2-aminothiazol-4-yl)-2-(R,S-carboxyeth-1-oxyimino)acetamido]-3-(2,6-diamino-3-methylpyrimidinium-4-yl)thiomethyl-3-cephem-4-carboxylate (I-3)

To a solution of 500 mg of (6R,7R)-3-acetoxymethyl-7[(Z)-2-(2-aminothiazol-4-yl)-2-(R,S-carboxyeth-1-oxyimino)acetamido]-3-cephem-4-carboxylic hydrochloride suspended in 5 ml of distilled water were added 200 mg of the title compound of Preparation Example 1 and 800 mg of potassium iodide. Subsequently, the same procedures as Example 1 were repeated to obtain 310 mg the title compound having the characteristics of:

m.p.>158° C.(dec.)

NMR(δ, D2O): 7.00(s, 1H), 6.20(s, 1H), 5.80(d, 1H), 5.19(d, 1H), 4.23(ABq, 2H), 3.55(ABq, 2H), 3.50(s, 3H), 1.43(d, 3H)

IR(KBr, cm$^{-1}$): 1760(β-lactam), 1669, 1612

EXAMPLE 4

Synthesis of (6R,7R)-7-[(Z)-2-(2-aminothiazol-4-yl)-2-(R,S-carboxyeth-1-oxyimino)acetamido]-3-(2,6-diamino-3-ethylpyrimidinium-4-yl)thiomethyl-3-cephem-4-carboxylate (I-4)

To a solution of 500 mg of (6R,7R)-3-acetoxymethyl-7[(Z)-2-(2-aminothiazol-4-yl)-2-(R,S-carboxyeth-1-oxyimino)acetamido]-3-cephem-4-carboxylic hydrochloride suspended in 5 ml of distilled water were added 300 mg of the title compound of Preparation Example 2 and 800 mg of potassium iodide. Subsequently, the same procedures as Example 1 were repeated to obtain 290 mg of the title compound having the characteristics of:

m.p.>160° C.(dec.)

NMR(δ, D2O): 7.00(s, 1H), 6.21(s, 1H), 5.81(d, 1H), 5.22(d, 1H), 4.21(ABq, 2H), 3.56(ABq, 2H), 4.01(q, 2H), 1.51(d, 3H), 1.40(t, 3H)

IR(KBr, cm$^{-1}$): 1765(β-lactam), 1670, 1615

EXAMPLE 5

Synthesis of (6R,7R)-7-[(Z)-2-(5-amino-1,2,4-thiadiazol-3-yl)-2-(ethoxyimino)acetamido]-3-(2,6-diamino-3-methylpyrimidinium-4-yl)thiomethyl-3-cephem-4-carboxylate(I-5)

To a solution of 500 mg of (6R,7R)-3-acetoxymethyl-7[(Z)-2-(5-amino-1,2,4-thiadiazol-3-yl)-2-(ethoxyimino)acetamido]-3-cephem-4-carboxylic hydrochloride suspended in 5 ml of distilled water were added 300 mg of the title compound of Preparation Example 1 and 800 mg of potassium iodide. Subsequently, the same procedures as Example 1 were repeated to obtain 300 mg the title compound having the characteristics of:

m.p. > 188° C.(dec.)

NMR(δ, D$_2$O): 6.21(s, 1H), 5.90(d, 1H), 5.22(d, 1H), 4.34(q, 2H), 3.6~4.1(dd, 2H), 3.45~4.85(dd, 2H), 3.56(s, 3H), 1.35(t, 3H)

IR(KBr, cm$^{-1}$): 1768(β-lactam), 1676

EXAMPLE 6

Synthesis of (6R,7R)-7-[(Z)-2-(5-amino-1,2,4-thiadiazol-3-yl)-2-(ethoxyimino)acetamido]-3-(2,6-diamino-3-ethyl-pyrimidinium-4-yl)thiomethyl-3-cephem-4-carboxylate (I-6)

To a solution of 500 mg of (6R,7R)-3-acetoxymethyl-7[(Z)-2-(5-amino-1,2,4-thiadiazol-3-yl)-2-(ethoxyimino)acetamido]-3-cephem-4-carboxylic hydrochloride suspended in 5 ml of distilled water were added 320 mg of the title compound of Preparation Example 2 and 800 mg of potassium iodide. Subsequently, the same procedures as Example 1 were repeated to obtain 280 mg the title compound having the characteristics of:

m.p. > 187° C.(dec.)

NMR(δ, D$_2$O): 6.20(s, 1H), 5.88(d, 1H), 5.22(d, 1H), 4.35(q, 2H), 3.88(q, 2H), 3.6~4.1(dd, 2H), 3.4~4.8(dd, 2H), 1.36(m, 6H)

IR(KBr, cm$^{-1}$): 1769(β-lactam), 1680, 1590

EXAMPLE 7

Synthesis of (6R,7R)-7-[(Z)-2-(2-aminothiazol-4-yl)-2-(methoxyimino)acetamido]-3-(2,6-diamino-3-methylpyrimidinium-4-yl)thiomethyl-3-cephem-4-carboxylate(I-7)

To a solution of 500 mg of (6R,7R)-3-acetoxymethyl-7[(Z)-2-(2-aminothiazol-4-yl)-2-(methoxyimino)acetamido]-3-cephem-4-carboxylic hydrochloride suspended in 10 ml of distilled water were added 200 mg of the title compound of Preparation Example 1 and 800 mg of potassium iodide. Subsequently, the same procedures as Example 1 were repeated to obtain 350 mg the title compound having the characteristics of:

m.p. > 160° C.(dec.)

NMR(δ, D$_2$O): 6.99(s, 1H), 6.22(s, 1H), 5.82(d, 1H), 5.18(d, 1H), 4.30(ABq, 2H), 4.01(s, 1H), 3.45(ABq, 2H), 3.60(s, 3H)

IR(KBr, cm$^{-1}$): 1762(β-lactam), 1620

EXAMPLE 8

Synthesis of (6R,7R)-7-[(Z)-2-(2-aminothiazol-4-yl)-2-(methoxyimino)acetamido]-3-(2,6-diamino-3-ethylpyrimidinium-4-yl)thiomethyl-3-cephem-4-carboxylate(I-8)

To a solution of 500 mg of (6R,7R)-3-acetoxymethyl-7[(Z)-2-(2-aminothiazol-4-yl)-2-(methoxyimino)acetamido]-3-cephem-4-carboxylic hydrochloride suspended in 10 ml of distilled water were added 300 mg of the title compound of Preparation Example 2 and 800 mg of potassium iodide. Subsequently, the same procedures as Example 1 were repeated to obtain 260 mg the title compound having the characteristics of:

m.p. > 165° C.(dec.)

NMR(δ,D$_2$O): 7.00(s, 1H), 6.21(s, 1H), 5.83(d, 1H), 5.19(d, 1H), 4.31(ABq, 2H), 3.95(q, 2H), 3.47(ABq, 2H), 3.80(s, 3H), 1.42(t, 3H)

EXAMPLE 9

Synthesis of (6R,7R)-7-[(Z)-2-(2-aminothiazol-4-yl)-2-(2-propyn-1-oxyimino)acetamido]-3-(2,6-diamino-3-methyl-pyrimidinium-4-yl)thiomethyl-3-cephem-4-carboxylate(I-9)

To a solution of 500 mg of (6R,7R)-3-acetoxymethyl-7[(Z)-2-(2-aminothiazol-4-yl)-2-(2-propyn-1-oxyimino)acetamido]-3-cephem-4-carboxylic hydrochloride suspended in 5 ml of distilled water were added 310 mg of the title compound of Preparation Example 1 and 800 mg of potassium iodide. Subsequently, the same procedures as Example 1 were repeated to obtain 270 mg the title compound having the characteristics of:

m.p. > 168° C.(dec.)

NMR(δ, D$_2$O): 7.00(s, 1H), 6.18(s, 1H), 5.85(d, 1H), 5.24(d, 1H), 4.82(s, 2H), 3.8~4.4(dd, 2H), 3.3~4.2(dd, 2H), 4.10(q, 2H), 3.90(s, 1H), 1.41(t, 3H)

IR(KBr, cm$^{-1}$): 1760(β-lactam), 1670

EXAMPLE 10

Synthesis of (6R,7R)-7-[(Z)-2-(5-amino-1,2,4-thiadiazol-3-yl)-2-(ethoxyimino)acetamido]-3-(2,6-diamino-1-methyl-pyrimidinium-4-yl)thiomethyl-3-cephem-4-carboxylate (I-11)

To a solution of 500 mg of (6R,7R)-3-acetoxymethyl-7-[(Z)-2-(5-amino-1,2,4-thiadiazol-3-yl)-2-(ethoxyimino)acetamido]-3-cephem-4-carboxylic hydrochloride suspended in 5 ml of distilled water were added 300 mg of the title compound of Preparation Example 3 and 800 mg of potassium iodide. Subsequently, the same procedures as Example 1 were repeated to obtain 300 mg of the desired title compound having the characteristics of:

m.p. > 158° C. (dec.)

NMR(δ, D$_2$O): 6.21(s, 1H), 5.83(d, 1H), 5.19(d, 1H), 4.34 (q, 2H), 3.6~4.1(dd, 2H), 3.45~4.85(dd, 2H), 3.64(s, 3H), 1.31(t, 3H)

IR(KBr, cm$^{-1}$): 1768(β-lactam), 1676

EXAMPLE 11

Synthesis of (6R,7R)-7-[(Z)-2-(5-amino-1,2,4-thiadiazol-3-yl)-2-(ethoxyimino)acetamido]-3-(2,6-diamino-1-ethyl-pyrimidinium-4-yl)thiomethyl-3-cephem-4-carboxylate (I-11)

To a solution of 500 mg of (6R,7R)-3-acetoxymethyl-7-[(Z)-2-(5-amino-1,2,4-thiadiazol-3-yl)-2-(ethoxyimino)acetamido]-3-cephem-4-carboxylic hydrochloride suspended in 5 ml of distilled water were added 320 mg of the title compound of Preparation Example 4 and 800 mg of potassium iodide. Subsequently, the same procedures as Example 1 were repeated to obtain 280 mg of the desired title compound having the characteristics of:

m.p. > 161° C. (dec.)

NMR(δ, D$_2$O): 6.13(s, 1H), 5.82(d, 1H), 5.20(d, 1H), 4.10 (q, 2H), 4.35(q, 2H), 3.6~4.1(dd, 2H), 3.4~4.8(dd, 2H), 1.36(m, 6H)

IR(KBr, cm$^{-1}$): 1769(β-lactam), 1680, 1590

EXAMPLE 12

Synthesis of
(6R,7R)-7-[(Z)-2-(2-aminothiazol-4-yl)-2-(carboxyprop-2-oxyimino)acetamido]-3-(2,6-diamino-1-methyl-pyrimidinium-4-yl)thiomethyl-3-cephem-4-carboxylate
(I-12)

To a solution of 500 mg of (6R,7R)-3-acetoxymethyl-7-[(Z)-2-(2-aminothiazol-4-yl)-2-(carboxyprop-2-oxyimino)acetamido]-3-cephem-4-carboxylic hydrochloride suspended in 5 ml of distilled water were added 200 mg of the title compound of Preparation Example 3 and 800 mg of potassium iodide. Subsequently, the same procedures as Example 1 were repeated to obtain 330 mg of the desired title compound having the characteristics of:

m.p. >175° C. (dec.)

NMR($\delta$, $D_2O$): 6.99(s, 1H), 6.19(s, 1H), 5.78(d, 1H), 5.20 (d, 1H), 3.6~4.3(dd, 2H), 3.4~4.0(dd, 2H), 3.61(s, 3H), 1.49(s, 6H)

IR(KBr, $cm^{-1}$): 1766($\beta$-lactam), 1669, 1615, 1558

EXAMPLE 13

Synthesis of
(6R,7R)-7-[(Z)-2-(2-aminothiazol-4-yl)-2-(carboxyprop-2-oxyimino)acetamido]-3-(2,6-diamino-1-ethyl-pyrimidinium-4-yl)thiomethyl-3-cephem-4-carboxylate
(I-13)

To a solution of 500 mg of (6R,7R)-3-acetoxymethyl-7-[(Z)-2-(2-aminothiazol-4-yl)-2-(carboxyprop-2-oxyimino)acetamido]-3-cephem-4-carboxylic hydrochloride suspended in 5 ml of distilled water were added 210 mg of the title compound of Preparation Example 4 and 800 mg of potassium iodide. Subsequently, the same procedures as Example 1 were repeated to obtain 300 mg of the desired title compound having the characteristics of:

m.p. >163° C. (dec.)

NMR($\delta$, $D_2O$): 6.99(s, 1H), 6.20(s, 1H), 5.78(d, 1H), 5.20 (d, 1H), 3.7~4.3(dd, 1H), 3.41~4.05(dd, 1H), 3.61(q, 2H), 1.52(s, 6H), 1.21(t, 3H)

IR(KBr, $cm^{-1}$): 1770($\beta$-lactam), 1680, 1590

EXAMPLE 14

Synthesis of
(6R,7R)-7-[(Z)-2-(2-aminothiazol-4-yl)-2-(2-propyn-1-oxyimino)acetamido]-3-(2,6-diamino-1-methyl-pyrimidinium-4-yl)thiomethyl-3-cephem-4-carboxylate
(I-14)

To a solution of 500 mg of (6R,7R)-3-acetoxymethyl-7-[(Z)-2-(2-aminothiazol-4-yl)-2-(2-propyn-1-oxyimino)acetamido]-3-cephem-4-carboxylic hydrochloride suspended in 5 ml of distilled water were added 300 mg of the title compound of Preparation Example 3 and 800 mg of potassium iodide. Subsequently, the same procedures as Example 1 were repeated to obtain 280 mg of the desired title compound having the characteristics of:

m.p. >167° C. (dec.)

NMR($\delta$, $D_2O$): 7.01(s, 1H), 6.24(s, 1H), 5.80(d, 1H), 5.20 (d, 1H), 4.81(s, 2H), 3.8~4.4(dd, 1H), 3.3~4.18(dd, 2H), 3.62(s, 3H), 3.08(s, 1H)

IR(KBr, $cm^{-1}$): 1770($\beta$-lactam), 1680, 1588

EXAMPLE 15

Synthesis of
(6R,7R)-7-[(Z)-2-(2-aminothiazol-4-yl)-2-(2-propyn-1-oxyimino)acetamido]-3-(2,6-diamino-1-ethylpyrimidinium-4-yl)thiomethyl-3-cephem-4-carboxylate (I-15)

To a solution of 500 mg of (6R,7R)-3-acetoxymethyl-7-[(Z)-2-(2-aminothiazol-4-yl)-2-(2-propyn-1-oxyimino)acetamido]-3-cephem-4-carboxylic hydrochloride suspended in 5 ml of distilled water were added 310 mg of the title compound of Preparation Example 4 and 800 mg of potassium iodide. Subsequently, the same procedures as Example 1 were repeated to obtain 270 mg of the desired title compound having the characteristics of:

m.p. >158° C. (dec.)

NMR($\delta$, $D_2O$): 7.00(d, 1H), 6.31(s, 1H), 5.85(d, 1H), 5.24 (d, 1H), 4.82(s, 2H), 3.8~4.4(dd, 2H), 3.3~4.2(dd, 2H), 3.09(s, 1H), 1.41(t, 3H)

IR(KBr, $cm^{-1}$): 1760($\beta$-lactam), 1670

EXAMPLE 16

Synthesis of
(6R,7R)-7-[(Z)-2-(5-aminothiazol-4-yl)-2-(2-propyn-1-oxyimino)acetamido]-3-(2,6-diamino-1-methyl-pyrimidinium-4-yl)thiomethyl-3-cephem-4-carboxylate
(I-16)

To a solution of 400 mg of (6R,7R)-3-acetoxymethyl-7-[(Z)-2-(2-aminothiazol-4-yl)-2-(2-propen-1-oxyimino)acetamido]-3-cephem-4-carboxylic hydrochloride suspended in 10 ml of distilled water were added 200 mg of the title compound of Preparation Example 3 and 800 mg of potassium iodide. Subsequently, the same procedures as Example 1 were repeated to obtain 180 mg of the desired title compound having the characteristics of:

m.p. >168° C. (dec.)

NMR($\delta$, $D_2O$): 6.96(s, 1H), 5.11~6.25(m, 5H), 6.32(s, 1H), 5.84(d, 1H), 5.19(d, 1H), 4.40(ABq, 2H), 3.61(ABq, 2H), 3.65(s, 3H)

IR(KBr, $cm^{-1}$): 1769($\beta$-lactam), 1671, 1619

EXAMPLE 17

Synthesis of
(6R,7R)-7-[(Z)-2-(2-aminothiazol-4-yl)-2-(carboxymethoxyimino)acetamido]-3-(2,6-diamino-1-methyl-pyrimidinium-4-yl)thiomethyl-3-cephem-4-carboxylate
(I-17)

To a solution of 400 mg of (6R,7R)-3-acetoxymethyl-7-[(Z)-2-(2-aminothiazol-4-yl)-2-(carboxymethoxyimino)acetamido]-3-cephem-4-carboxylic hydrochloride suspended in 5 ml of distilled water were added 200 mg of the title compound of Preparation Example 3 and 800 mg of potassium iodide. Subsequently, the same procedures as Example 1 were repeated to obtain 200 mg of the desired title compound having the characteristics of:

m.p. >158° C.(dec.)

NMR($\delta$, $D_2O$): 7.01(s, 1H), 6.28(s, 1H), 5.79(d, 1H), 5.22 (d, 1H), 4.55(s, 2H), 4.20(ABq), 3.52(ABq), 3.58(s, 3H)

IR(KBr, $cm^{-1}$): 1766($\beta$-lactam), 1675, 1610

EXAMPLE 18

Synthesis of
(6R,7R)-7-[(Z)-2-(2-aminothiazol-4-yl)-2-(carboxymethoxyimino)acetamido]-3-(2,6-diamino-1-ethylpryrimidinium-4-yl)thiomethyl-3-cephem-4-carboxylate (I-18)

To a solution of 400 mg of (6R,7R)-3-acetoxymethyl-7-[(Z)-2-(2-aminothiazol-4-yl)-2-(carboxymethoxyimino)acetamido]-3-cephem-4-carboxylic hydrochloride suspended in 5 ml of distilled water were added 250 mg of the title compound of Preparation Example 4 and 800 mg of potassium iodide. Subsequently, the same procedures as Example 1 were repeated to obtain 185 mg of the desired title compound having the characteristics of:

m.p. > 165° C.(dec.)

NMR($\delta$, $D_2O$): 7.00(s, 1H), 6.28(s, 1H), 5.80(d, 1H), 5.21 (d, 1H), 4.56(s, 2H), 4.20(ABq), 4.12(q, 2H), 1.42(t, 3H)

IR(KBr, $cm^{-1}$): 1762($\beta$-lactam), 1668, 1610

EXAMPLE 19

Synthesis of
(6R,7R)-7-[(Z)-2-(2-aminothiazol-4-yl)-2-(R,S-carboxyeth-1-oxyimino)acetamido]-3-(2,6-diamino-1-methylpyrimidinium-4-yl)thiomethyl-3-cephem-4-carboxylate(I-19)

To a solution of 500 mg of (6R,7R)-3-acetoxymethyl-7-[(Z)-2-(2-aminothiazol-4-yl)-2-(R,S-carboxyeth-1-oxyimino)acetamido]-3-cephem-4-carboxylic hydrochloride suspended in 5 m of distilled water were added 200 mg of the title compound of Preparation Example 3 and 800 mg of potassium iodide. Subsequently, the same procedures as Example 1 were repeated to obtain 310 mg of the desired title compound having the characteristics of:

m.p. > 165° C.(dec.)

NMR($\delta$, $D_2O$): 7.01(s, 1H), 6.29(s, 1H), 5.80(d, 1H), 5.23 (d, 1H), 4.23(ABq, 2H), 3.55(ABq, 2H), 3.75(s, 3H), 1.43 (d, 3H)

IR(KBr, $cm^{-1}$): 1760($\beta$-lactam), 1669, 1612

EXAMPLE 20

Synthesis of
(6R,7R)-7-[(Z)-2-(2-aminothiazol-4-yl)-2-(R,S-carboxyeth-1-oxyimino)acetamido]-3-(2,6-diamino-1-ethylprimidinium-4-yl)thiomethyl-3cephem-4-carboxylate (I-20)

To a solution of 500 mg of (6R,7R)-3-acetoxymethyl-7-[(Z)-2-(2-aminothiazol-4-yl)-2-(R,S-carboxyeth-1-oxyimino)acetamido]-3-cephem-4-carboxylic hydrochloride suspended in 5 ml of distilled water were added 300 mg of the title compound of Preparation Example 4 and 800 mg of potassium iodide. Subsequently, the same procedures as Example 1 were repeated to obtain 290 mg of the desired title compound having the characteristics of:

m.p. > 168° C.(dec.)

NMR($\delta$, $D_2O$): 7.00(s, 1H), 6.28(s, 1H), 5.81(d, 1H), 5.22 (d, 1H), 4.21(ABq, 2H), 3.56(ABq, 2H), 4.21(q, 2H), 1.51 (d, 3H), 1.40(t, 3H)

IR(KBr, $cm^{-1}$): 1765($\beta$-lactam), 1670, 1615

EXAMPLE 21

Synthesis of
(6R,7R)-7-[(Z)-2-(2-aminothiazol-4-yl)-2-(methoxyimino)acetamido]-3-(2,6-diamino-1-methylpyrimidinium-4-yl)thiomethyl-3-cephem-4-carboxylate (I-21)

To a solution of 500 mg of (6R,7R)-3-acetoxymethyl-7-[(Z)-2-(2-aminothiazol-4-yl)-2-(methoxyimino)acetamido]-3-cephem-4-carboxylic hydrochloride suspended in 10 ml of distilled water were added 200 mg of the title compound of Preparation Example 3 and 800 mg of potassium iodide. Subsequently, the same procedures as Example 1 were repeated to obtain 350 mg of the title compound having the characteristics of:

m.p. > 158° C.(dec.)

NHR($\delta$, $D_2O$): 7.02(s, 1H), 6.29(s, 1H), 5.82(d, 1H), 5.22 (d, 1H), 4.30(ABq, 2H), 3.80(s, 1H), 3.45(ABq, 2H), 3.58 (s, 3H)

IR(KBr, $cm^{-1}$): 1762($\beta$-lactam), 1620

EXAMPLE 22

Synthesis of
(6R,7)-7-[(Z)-2-(2-aminothiazol-4-yl)-2-(methoxyimino)acetamido]-3-(2,6-diamino-1-ethylpyrimidinium-4-yl)thiomethyl-3-cephem-4-carboxylate (I-22)

To a solution of 500 mg of (6R,7R)-3-acetoxymethyl-7-[(Z)-2-(2-aminothiazol-4-yl)-2-(methoxyimino)acetamido]-3-cephem-4-carboxylic hydrochloride suspended in 10 ml of distilled water were added 300 mg of the title compound of Preparation Example 4 and 800 mg of potassium iodide. Subsequently, the same procedures as Example 1 were repeated to obtain 260 mg of the title compound having the characteristics of:

m.p. > 161° C.(dec.)

NMR($\delta$, $D_2O$): 7.00(s, 1H), 6.29(s, 1H), 5.83(d, 1H), 5.23 (d, 1H), 4.31(ABq, 2H), 4.25q, 2H), 3.47(ABq, 2H), 3.80 (s, 3H), 1.42(t, 3H)

IR(KBr, $cm^{-1}$): 1770($\beta$-lactam), 1672

EXAMPLE 23

Synthesis of
7-[(Z)-2-(2-aminothiazol-4-yl)-2-(2-carboxyprop-2-oxyimino)acetamido]-3-(4,6-diamino-1-methyl-1,3,5-triazinium-2-yl)thiomethyl-3-cephem-4-carboxylate(I-23)

To a solution of 500 mg of 3-acetoxymethyl-7-[(Z)-2-(2-aminothiazol-4-yl)-2-(2-carboxyprop-2-oxyimino)acetamido]-3-cephem-4-carboxylic hydrochloride dissolved in 10 ml of distilled water were added 200 mg of the title compound of preparation Example 5 and 1200 mg of potassium chloride. The reaction solution was heated to 70° C., while the pH was adjusted to 7.3 to 7.5 with addition of aqueous sodium bicarbonate solution. The solution was stirred for 4 hours, cooled to a room temperature, adjusted pH to 4 and concentrated under the reduced pressure.

The residues were fractionated on the chromatography on silica gel using mixtures of acetonitrile and distilled water (4:1) as an eluent to obtain 150 mg of the title compound as light yellow solid having the characteristics of:

m.p. > 185° C.(dec.)

NMR($\delta$, $D_2O$+$NaHCO_3$): 1.44(s, 6H), 3.41(ABq, 2H), 3.70 (s, 3H), 4.32(ABq, 2H), 5.18(d, 1H), 5.71(d, 1H), 6.92(s, 1H)

IR(KCl, $cm^{-1}$): 3300, 3200(N—H), 1760(C=O)

EXAMPLE 24

Synthesis of 7-[(Z)-2-(2-aminothiazol-4-yl)-2-(2-carboxyprop-2-oxyimino)acetamido]-3-(4,6-diamino-1-ethyl-1,3,5-triazinium-2-yl)thiomethyl-3-cephem-4-carboxylate(I-24)

The procedures of Example 23 were repeated except that the title compound of Preparation Example 5 was substituted with one of Preparation Example 6 to obtain 170 mg of the desired title compound having the characteristics of:

m.p. > 192° C.(dec.)

NMR(δ, D$_2$O+NaHCO$_3$): 1.31(t, 3H), 1.45(d, 6H), 3.56(ABq, 2H), 4.00(q, 2H), 4.46(q, 2H), 5.12(d, 1H), 5.78(d, 1H), 6.93(s, 1H)

IR(KCl, cm$^{-1}$): 3280, 3190(N—H), 1759(C=O)

EXAMPLE 25

Synthesis of 7-[(Z)-2-(2-aminothiazol-4-yl)-2-(2-carboxyprop-2-oxyimino)acetamido]-3-(4,6-diamino-1-phenyl-1,3,5-triazinium-2-yl)thiomethyl-3-cephem-4-carboxylate(I-25)

The procedures of Example 23 were repeated except that the title compound of Preparation Example 5 was substituted with one of Preparation Example 7 to obtain 180 mg of the desired title compound having the characteristics of:

m.p. > 205° C.(dec.)

NMR(δ, D$_2$O+NaHCO$_3$): 1.46(s, 6H), 3.48(ABq, 2H), 4.25(ABq, 2H), 5.16(d, 1H), 5.78(d, 1H), 6.90(s, 1H), 7.4~7.7(m, 5H)

IR(KCl, cm$^{-1}$): 3320, 3210(N—H), 1761(C=O)

In order to illustrate their surprisingly superior antibacterial effectiveness, the minimal inhibitory concentrations (MIC) of the 27 compounds synthesized in Examples 1 through 27 against standard strains were determined and compared with Ceftazidime of formula(C) and Cefotaxime of formula(X), which were used as the control compounds.

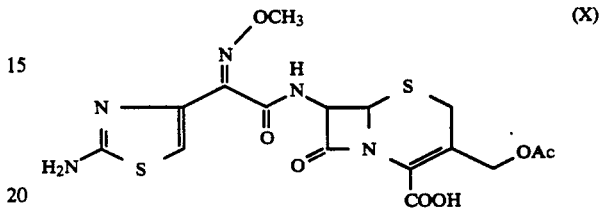

These MIC values were taken by employing a two-fold dilution method: that is, two-fold serial dilutions of each of the test compounds were made and dispersed in a Muller-Hinton agar medium; 2 μl of the standard test strain which had the 10$^7$ CFU(Colony Forming Unit) per ml was inoculated on the medium; and these were incubated at 37° C. for 20 hours. The results of the MIC tests are shown Table 1.

TABLE 1

(Antibacterial Activity MIC, μg/ml)

| Strain | Compound | I-1 | I-2 | I-3 | I-4 | I-5 | I-6 | I-7 |
|---|---|---|---|---|---|---|---|---|
| Bacillus cereus | ATCC 11778 | 128 | 64 | 64 | 64 | 64 | 64 | 64 |
| Bacillus megaterium | ATCC 9885 | 0.25 | 0.25 | 0.25 | 0.25 | 0.13 | 0.13 | 0.13 |
| Micrococcus luteus | ATCC 9341 | 0.5 | 0.5 | 0.5 | 0.5 | 0.031 | 0.063 | 0.063 |
| Staphylococcus aureus | ATCC 6538p | 8 | 4 | 4 | 8 | 2 | 1 | 2 |
| Staphylococcus aureus | ATCC 10537 | 4 | 4 | 4 | 4 | 1 | 1 | 1 |
| Staphylococcus epidermidis | ATCC 12228 | 2 | 1 | 2 | 1 | 0.5 | 0.5 | 0.5 |
| Streptococcus faecalis | ATCC 29212 | >128 | >128 | >128 | >128 | >128 | >128 | >128 |
| Acinetobacter calcoaceticus | ATCC 15473 | 4 | 4 | 2 | 4 | 8 | 8 | 8 |
| Citrobacter freundii | ATCC 8090 | 0.13 | 0.13 | 0.13 | 0.13 | 0.25 | 0.13 | 0.25 |
| Enterobacter aerogenes | ATCC 29751 | 2 | 1 | 2 | 1 | 0.5 | 0.5 | 0.5 |
| Enterobacter cloacae | ATCC 27508 | 0.016 | 0.016 | 0.016 | 0.016 | 0.016 | 0.063 | 0.016 |
| Escherichia coli | ATCC 10536 | 0.13 | 0.063 | 0.13 | 0.13 | 0.13 | 0.13 | 0.13 |
| Escherichia coli | ATCC 25922 | 0.13 | 0.063 | 0.13 | 0.13 | 0.13 | 0.13 | 0.13 |
| Klebsiella pneumoniae | ATCC 10031 | 0.031 | 0.031 | 0.031 | 0.031 | 0.016 | 0.031 | 0.016 |
| Morganella morganii | ATCC 8076h | <=0.008 | <=0.008 | <=0.008 | <=0.008 | <=0.008 | <=0.008 | 0.016 |
| Proteus mirabilis | ATCC 25933 | 0.31 | 0.31 | 0.31 | 0.31 | 0.061 | 0.016 | 0.031 |
| Proteus vulgaris | ATCC 6059 | 0.31 | 0.13 | 0.063 | 0.063 | 0.031 | 0.031 | 0.063 |
| Providencia rettgeri | ATCC 9250 | <=0.008 | <=0.008 | <=0.008 | <=0.008 | <=0.008 | <=0.008 | <=0.008 |
| Salmonella typhimurium | ATCC 14028 | 0.5 | 0.5 | 0.5 | 0.5 | 0.5 | 0.5 | 1 |
| Serratia marcescens | ATCC 27117 | 0.13 | 0.13 | 0.13 | 0.13 | 0.5 | 0.25 | 0.5 |
| Shigella flexneri | ATCC 11836 | 0.031 | 0.031 | 0.031 | 0.031 | 0.063 | 0.063 | 0.063 |
| Shigella sonnei | ATCC 11060 | 0.25 | 0.25 | 0.25 | 0.25 | 0.25 | 0.25 | 0.5 |
| Pseudomonas aeruginosa | ATCC 25619 | 1 | 1 | 1 | 1 | 2 | 2 | 2 |
| Pseudomonas aeruginosa | ATCC 27853 | 1 | 1 | 1 | 2 | 16 | 16 | 32 |
| Pseudomonas aeruginosa | ATCC 10145 | 2 | 1 | 1 | 2 | 32 | 16 | 64 |
| Strain | Compound | I-8 | I-9 | I-10 | I-11 | I-12 | I-13 | I-14 |
| Bacillus cereus | ATCC 11778 | 64 | 64 | 128 | 128 | 128 | 128 | 64 |
| Bacillus megaterium | ATCC 9885 | 0.13 | 0.13 | 0.13 | 0.13 | 0.25 | 0.25 | 0.25 |
| Micrococcus luteus | ATCC 9341 | 0.063 | 0.063 | 0.016 | 0.016 | 0.5 | 0.5 | 0.031 |
| Staphylococcus aureus | ATCC 6538p | 2 | 0.25 | 0.5 | 0.5 | 8 | 8 | 0.5 |
| Staphylococcus aureus | ATCC 10537 | 1 | 0.25 | 0.5 | 0.5 | 4 | 4 | 0.5 |
| Staphylococcus epidermidis | ATCC 12228 | 0.5 | 0.5 | 0.25 | 0.25 | 4 | 2 | 0.25 |
| Streptococcus faecalis | ATCC 29212 | >128 | >128 | 8 | 8 | >128 | >128 | 16 |
| Acinetobacter calcoaceticus | ATCC 15473 | 8 | 2 | 4 | 4 | 8 | 8 | 8 |
| Citrobacter freundii | ATCC 8090 | 0.13 | 0.13 | 0.13 | 0.063 | 0.13 | 0.13 | 0.25 |
| Enterobacter aerogenes | ATCC 29751 | 0.5 | 0.5 | 0.25 | 0.13 | 2 | 2 | 0.5 |
| Enterobacter cloacae | ATCC 27508 | 0.016 | 0.13 | 0.016 | <=0.008 | 0.031 | 0.031 | 0.016 |
| Escherichia coli | ATCC 10536 | 0.063 | 0.016 | 0.13 | 0.13 | 0.25 | 0.13 | 0.5 |
| Escherichia coli | ATCC 25922 | 0.063 | 0.063 | 0.25 | 0.25 | 0.25 | 0.13 | 0.25 |
| Klebsiella pneumoniae | ATCC 10031 | 0.016 | 0.063 | <=0.008 | <=0.008 | 0.063 | 0.063 | 0.016 |
| Morganella morganii | ATCC 8076h | 0.016 | <=0.008 | 0.016 | 0.016 | <=0.008 | <=0.008 | 0.016 |
| Proteus mirabilis | ATCC 25933 | 0.031 | 0.016 | 0.25 | 0.5 | 0.13 | 0.13 | 1 |

TABLE 1-continued
(Antibacterial Activity MIC, μg/ml)

| Strain | | | | | | | |
|---|---|---|---|---|---|---|---|
| Proteus vulgaris | ATCC 6059 | 0.063 | 0.016 | 0.25 | 0.5 | 0.25 | 0.25 | 1 |
| Providencia rettgeri | ATCC 9250 | <=0.008 | <=0.008 | <=0.008 | <=0.008 | <=0.008 | <=0.008 | <=0.008 |
| Salmonella typhimurium | ATCC 14028 | 0.5 | 0.5 | 0.063 | 0.063 | 0.25 | 0.25 | 0.25 |
| Serratia marcescens | ATCC 27117 | 0.5 | 0.5 | 0.13 | 0.13 | 0.5 | 0.5 | 0.5 |
| Shigella flexneri | ATCC 11836 | 0.063 | 0.13 | 0.031 | 0.031 | 0.063 | 0.063 | 0.063 |
| Shigella sonnei | ATCC 11060 | 0.5 | 0.13 | 0.25 | 0.25 | 0.25 | 0.25 | 0.5 |
| Pseudomonas aeruginosa | ATCC 25619 | 2 | 2 | 0.5 | 0.5 | 1 | 1 | 1 |
| Pseudomonas aeruginosa | ATCC 27853 | 16 | 8 | 1 | 1 | 1 | 1 | 4 |
| Pseudomonas aeruginosa | ATCC 10145 | 32 | 16 | 1 | 2 | 2 | 2 | 8 |

| Strain | Compound | I-15 | I-16 | I-17 | I-18 | I-19 | I-20 | I-21 |
|---|---|---|---|---|---|---|---|---|
| Bacillus cereus | ATCC 11778 | 32 | 64 | >128 | >128 | 128 | 128 | 128 |
| Bacillus megaterium | ATCC 9885 | 0.25 | 0.25 | 0.5 | 0.5 | 0.25 | 0.25 | 0.13 |
| Micrococcus luteus | ATCC 9341 | 0.031 | 0.031 | 1 | 0.5 | 0.5 | 0.25 | 0.063 |
| Staphylococcus aureus | ATCC 6538p | 0.5 | 0.5 | 8 | 4 | 4 | 2 | 0.5 |
| Staphylococcus aureus | ATCC 10537 | 0.5 | 0.5 | 4 | 4 | 4 | 4 | 0.5 |
| Staphylococcus epidermidis | ATCC 12228 | 0.25 | 0.25 | 2 | 2 | 4 | 4 | 0.25 |
| Streptococcus faecalis | ATCC 29212 | 16 | 32 | >128 | >128 | 128 | 128 | 32 |
| Acinetobacter calcoaceticus | ATCC 15473 | 8 | 8 | 16 | 16 | 8 | 8 | 8 |
| Citrobacter freundii | ATCC 8090 | 0.25 | 0.25 | 0.031 | 0.063 | 0.13 | 0.13 | 0.031 |
| Enterobacter aerogenes | ATCC 29751 | 1 | 1 | 1 | 2 | 1 | 1 | 0.25 |
| Enterobacter cloacae | ATCC 27508 | 0.031 | 0.063 | 0.016 | 0.016 | 0.031 | 0.016 | <=0.008 |
| Escherichia coli | ATCC 10536 | 0.25 | 0.5 | 0.031 | 0.063 | 0.13 | 0.13 | 0.063 |
| Escherichia coli | ATCC 25922 | 0.5 | 0.5 | 0.016 | 0.063 | 0.13 | 0.13 | 0.063 |
| Klebsiella pneumoniae | ATCC 10031 | 0.016 | 0.016 | 0.031 | 0.031 | 0.063 | 0.063 | <=0.008 |
| Morganella morganii | ATCC 8076h | 0.016 | 0.016 | <=0.008 | <=0.008 | <=0.008 | <=0.008 | <=0.008 |
| Proteus mirabilis | ATCC 25933 | 0.5 | 1 | 0.031 | 0.063 | 0.13 | 0.063 | 0.5 |
| Proteus vulgaris | ATCC 6059 | 1 | 1 | 0.063 | 0.063 | 0.25 | 0.25 | 0.5 |
| Providencia rettgeri | ATCC 9250 | <=0.008 | <=0.008 | <=0.008 | <=0.008 | <=0.008 | <=0.008 | <=0.008 |
| Salmonella typhimurium | ATCC 14028 | 0.5 | 1 | 0.063 | 0.25 | 0.25 | 0.5 | 0.13 |
| Serratia marcescens | ATCC 27117 | 0.5 | 2 | 0.063 | 0.063 | 0.25 | 0.25 | 0.25 |
| Shigella flexneri | ATCC 11836 | 0.13 | 0.25 | 0.016 | 0.016 | 0.016 | 0.016 | 0.016 |
| Shigella sonnei | ATCC 11060 | 0.5 | 0.5 | 0.031 | 0.063 | 0.25 | 0.5 | 0.13 |
| Pseudomonas aeruginosa | ATCC 25619 | 1 | 2 | 1 | 1 | 1 | 1 | 1 |
| Pseudomonas aeruginosa | ATCC 27853 | 4 | 4 | 2 | 2 | 2 | 2 | 2 |
| Pseudomonas aeruginosa | ATCC 10145 | 8 | 8 | 4 | 4 | 4 | 4 | 16 |

| Strain | Compound | I-22 | I-23 | I-24 | I-25 | Ceftazidime | Cefotaxime |
|---|---|---|---|---|---|---|---|
| Bacillus cereus | ATCC 11778 | 64 | 128 | >128 | 128 | 128 | 64 |
| Bacillus megaterium | ATCC 9885 | 0.25 | 0.5 | 0.5 | 0.5 | 0.25 | 0.063 |
| Micrococcus luteus | ATCC 9341 | 0.031 | 1 | 1 | 0.5 | 1 | 0.031 |
| Staphylococcus aureus | ATCC 6538p | 0.25 | 8 | 4 | 4 | 16 | 4 |
| Staphylococcus aureus | ATCC 10537 | 0.5 | 2 | 2 | 4 | 8 | 1 |
| Staphylococcus epidermidis | ATCC 12228 | 0.25 | 2 | 2 | 4 | 8 | 1 |
| Streptococcus faecalis | ATCC 29212 | 8 | >128 | >128 | >128 | >128 | >128 |
| Acinetobacter calcoaceticus | ATCC 15473 | 8 | 4 | 4 | 16 | 4 | 8 |
| Citrobacter freundii | ATCC 8090 | 0.25 | 0.13 | 0.13 | 0.5 | 1 | 0.063 |
| Enterobacter aerogenes | ATCC 29751 | 0.25 | 2 | 2 | 2 | 4 | 2 |
| Enterobacter cloacae | ATCC 27508 | <=0.008 | 0.031 | 0.031 | 0.13 | 0.063 | <=0.008 |
| Escherichia coli | ATCC 10536 | 0.063 | 0.063 | 0.13 | 0.13 | 0.13 | 0.031 |
| Escherichia coli | ATCC 25922 | 0.063 | 0.063 | 0.063 | 0.25 | 0.13 | 0.031 |
| Klebsiella pneumoniae | ATCC 10031 | <=0.008 | 0.063 | 0.063 | 0.25 | 0.13 | <=0.008 |
| Morganella morganii | ATCC 8076h | <=0.008 | <=0.008 | <=0.008 | <=0.008 | 0.016 | <=0.008 |
| Proteus mirabilis | ATCC 25933 | 0.25 | 0.063 | 0.063 | 0.13 | 0.063 | 0.031 |
| Proteus vulgaris | ATCC 6059 | 0.25 | 0.063 | 0.063 | 0.13 | 0.063 | 0.031 |
| Providencia rettgeri | ATCC 9250 | <=0.008 | <=0.008 | <=0.008 | <=0.008 | <=0.008 | <=0.008 |
| Salmonella typhimurium | ATCC 14028 | 0.13 | 0.13 | 0.13 | 0.25 | 0.25 | 0.13 |
| Serratia marcescens | ATCC 27117 | 0.25 | 0.13 | 0.13 | 0.13 | 0.13 | 0.13 |
| Shigella flexneri | ATCC 11836 | 0.063 | 0.063 | 0.063 | 0.13 | 0.063 | 0.016 |
| Shigella sonnei | ATCC 11060 | 0.031 | 0.063 | 0.063 | 0.25 | 0.063 | 0.063 |
| Pseudomonas aeruginosa | ATCC 25619 | 1 | 1 | 1 | 1 | 1 | 1 |
| Pseudomonas aeruginosa | ATCC 27853 | 2 | 1 | 1 | 2 | 1 | 8 |
| Pseudomonas aeruginosa | ATCC 10145 | 8 | 2 | 2 | 4 | 2 | 16 |

We claim:

1. A cephalosporin compound of the formula (I) and its isomers and pharmaceutically acceptable non-toxic salts:

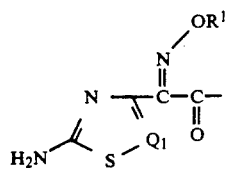

(I)

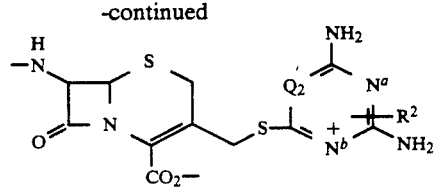

wherein:

$R^1$ is a $C_{1-4}$ alkyl, $C_{3-4}$ alkenyl, $C_{3-4}$ alkynyl or $-C(R^3)(R^4)COOH$ wherein $R^3$ and $R^4$, which may be the same or different, are a hydrogen or a $C_{1-4}$ alkyl group, or constitute a $C_{3-7}$ cycloalkyl group with the carbon atoms to which $R^3$ and $R^4$ are linked;

$R^2$, which may be attached to $N^a$ or $N^b$, is a $C_{1-4}$ alkyl, $C_{3-4}$ alkenyl, $C_{3-7}$ cycloalkyl, phenyl or amino group;

$Q_1$ is CH or N; and $Q_2$ is N.

2. The cephalosporin compound of claim 1 wherein the compound is 7-[(Z)-2-(2-aminothiazol-4-yl)-2-(2-carboxyprop-2-oxyimino)acetamido]-3-(4,6-diamino-1-methyl-1,3,5-triazinium-2-yl)thiomethyl-3-cephem-4-carboxylate.

3. The cephalosporin compound of claim 1 wherein the compound is 7-[(Z)-2-(2-aminothiazol-4-yl)-2-(2-carboxyprop-2-oxyimino)acetamido]-3-(4,6-diamino-1-ethyl-1,3,5-triazinium-2-yl)thiomethyl-3-cephem-4-carboxylate.

4. The cephalosporin compound of claim 1 wherein the compound is 7-[(Z)-2-(2-aminothiazol-4-yl)-2-(2carboxyprop-2-oxyimino)acetamido]-3-(4,6-diamino-1-phenyl-1,3,5-triazinium-2-yl)thiomethyl-3-cephem-4-carboxylate.

5. A pharmaceutical composition consisting essentially of a therapeutically effective amount of a cephalosporin compound of claim 1 and a pharmaceutically acceptable carrier.

* * * * *